(12) United States Patent
Campbell et al.

(10) Patent No.: US 6,304,327 B1
(45) Date of Patent: *Oct. 16, 2001

(54) METHOD AND APPARATUS FOR PHOTOMETRIC ANALYSIS OF CHLORINE DIOXIDE SOLUTIONS

(75) Inventors: Kurtland Scott Campbell; David August Hildebrand, both of Witchita, KS (US)

(73) Assignee: Vulcan Chemicals, Wichita, KS (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/260,801

(22) Filed: Mar. 2, 1999

(51) Int. Cl.[7] .................................................. G01N 21/61
(52) U.S. Cl. ............................................................ 356/437
(58) Field of Search .................................... 356/435, 437, 356/439

(56) References Cited

U.S. PATENT DOCUMENTS

| | | |
|---|---|---|
| 3,306,156 | 2/1967 | Glasser et al. . |
| 3,970,430 | * 7/1976 | Reader et al. ........................ 356/437 |
| 4,013,506 | 3/1977 | Histed et al. . |
| 4,128,454 | 12/1978 | Schleinkofer . |
| 4,152,073 | * 5/1979 | Zimmerman .......................... 356/436 |
| 4,311,485 | 1/1982 | Saltzman et al. . |

(List continued on next page.)

FOREIGN PATENT DOCUMENTS

| | | |
|---|---|---|
| 0 119 686 | 9/1984 | (EP) . |
| 0 211 073 | 2/1987 | (EP) . |
| 0 366 262 | 5/1990 | (EP) . |
| 0 510 277 | 10/1992 | (EP) . |
| 0 573 715 | 12/1993 | (EP) . |
| 2 395 504 | 1/1979 | (FR) . |
| 2 680 973 | 3/1993 | (FR) . |
| 2 031 613 | 4/1980 | (GB) . |
| 59-27249 | 2/1984 | (JP) . |
| 3-8503 | 1/1991 | (JP) . |
| 7-265867 | 10/1995 | (JP) . |
| 598843 | 3/1978 | (SU) . |
| 86/04698 | 8/1986 | (WO) . |
| 90/01457 | 2/1990 | (WO) . |
| 91/05998 | 5/1991 | (WO) . |
| 91/09690 | 7/1991 | (WO) . |
| 95/02965 | 2/1995 | (WO) . |

OTHER PUBLICATIONS

"Continuous Monitoring for Control of Chlorine Dioxide Generators", Robert S. Saltzman, pp. 1–4, 1975.

"Challenges in the Measurement of Chlorine Dioxide at Denver's Potable Water Reuse Demonstration Plant", Stephen R. Loman, et al., pp. 201–211.

(List continued on next page.)

Primary Examiner—Richard A. Rosenberger
(74) Attorney, Agent, or Firm—Burns, Doane, Swecker & Mathis, L.L.P.

(57) ABSTRACT

A novel method and apparatus for photometrically analyzing a dilute solution containing chlorine dioxide is provided. The method includes introducing a sample flow into a conduit of a chlorine dioxide analyzer. At least one light emitting diode, in communication with the sample flow, is turned on and off to pass a light beam through the sample. Upon passing through the light beam through the sample the unabsorbed light is received onto a beam splitter which separates the light into a transmitted and a reflected light. The transmitted light is directed through a filter to a first detector which measures the low concentration chlorine dioxide and the reflected light is directed to a second detector which measures a high concentration of chlorine dioxide.

29 Claims, 8 Drawing Sheets

U.S. PATENT DOCUMENTS

| | | |
|---|---|---|
| 4,324,635 | 4/1982 | Sweeney . |
| 4,542,008 | 9/1985 | Capuano et al. . |
| 4,555,491 | 11/1985 | Spurlin et al. . |
| 4,575,433 | 3/1986 | Spurlin et al. . |
| 4,634,574 | 1/1987 | Spurlin et al. . |
| 4,908,188 | 3/1990 | Jefferis, III et al. . |
| 4,921,675 | 5/1990 | Johnson . |
| 4,949,400 * | 8/1990 | Leveen et al. .................. 356/420 |
| 5,009,875 | 4/1991 | Kelley et al. . |
| 5,190,725 | 3/1993 | Meijer et al. . |
| 5,269,832 | 12/1993 | Meijer . |
| 5,279,673 | 1/1994 | Dziabo et al. . |
| 5,283,199 | 2/1994 | Bacon, Jr. et al. . |
| 5,336,434 | 8/1994 | Park et al. . |
| 5,366,605 | 11/1994 | Wang . |
| 5,382,520 | 1/1995 | Jenson et al. . |
| 5,389,390 | 2/1995 | Kross . |
| 5,660,874 | 8/1997 | Pitochelli et al. . |

OTHER PUBLICATIONS

"Continuous Monitoring for Control of Chlorine Dioxide Generators", Robert S. Saltzman, E.I. Du Pont de Nemours & Co., Inc. Instrument Products Division, pp. 609–1–3, 1975.

"Challenges in the Measurement of Chlorine Dioxide at Denver's Potable Water Reuse Demonstration Plant", Stephen R. Lohman, et al, Denver Water Department, pp. 201–211.

* cited by examiner

Chlorine Dioxide Analyzer
Electronics

Chlorine Dioxide Analyzer
Example 3
Electronics

METHOD AND APPARATUS FOR PHOTOMETRIC ANALYSIS OF CHLORINE DIOXIDE SOLUTIONS

BACKGROUND OF THE INVENTION

1. Field of the Invention

The present invention relates to photometric analysis, and in particular to a novel method and apparatus for photometrically measuring chlorine dioxide concentrations in a stream.

2. Description of Related Art

Chlorine dioxide in solutions at various concentrations is useful as a bleaching agent for pulp used in the manufacture of white paper, or to oxidize and disinfect in a variety of applications. One such notable application, is the treatment of drinking water where limited amounts of chlorinated chemicals such as sodium chlorite is desired.

In a chlorine dioxide generator, for example, the addition of the optimum quantities of sodium chlorite and chlorine results in a conversion to chlorine dioxide of almost 100% with almost non-detectable sodium chlorite and chlorine found therein. In order to meet the necessary safety standards and the stringent government regulations, it is of particular importance to detect changes in chlorine dioxide concentration and optimize the chlorine and sodium chlorite additions to achieve as high a rate of conversion to chlorine dioxide as possible.

On site generation of chlorine dioxide is common, as the solutions cannot be shipped or stored for long periods of time. Control of the generating process is needed to manufacture solutions with respective concentrations. The article "Continuous Monitoring for Control of Chlorine Dioxide Generators" written by R. S. Saltzman and published in "Instrumentation in the Pulp and Paper Industry," Volume 16, Section 609, Coden: IPPICO 16 (1975), Instruments Society of America, Research Triangle Park, North Carolina, describes a photometric analysis apparatus adapted to continuously monitor the output of a chlorine dioxide generator. These conventional analyzers employ incandescent light sources such as the ones disclosed in U.S. Pat. No. 4,152,073 (Zimmerman) issued on May 1, 1979 and U.S. Pat. No. 4,311,485 (Saltzman et al.) issued on Jan. 19, 1982).

Some of the disadvantages associated with these light sources is that they require more power, generate more heat and slowly deteriorate to the point of failure. Typically analyzers with incandescent light sources require warm up times of thirty minutes to a day. Therefore, the light is left in the on position to provide stability, and chopper wheels are utilized to obtain detector readings in the dark by blocking the light selectively.

Another drawback related to commercially available analyzers is that multiple interference filters, prisms, or gratings are necessary to generate monochromatic light beams. These types of interference filters are disclosed in U.S. Pat. No. 4,152,073 (Zimmerman) issued on May 1, 1979. In accordance with DeBeers law, monochromatic light is absorbed by chlorine dioxide and results in logarithmic changes in light intensity and detector responses.

To overcome the disadvantages of the prior art, it is an object of the present invention to provide an analyzer having blue and red light emitting sources (LED's) which can last up to ten years, provide a more stable light output and consume less energy (less than 76 mW). The analyzer allows the passing of light emitted from the blue diode directly through the chlorine dioxide solution and measures the response sensed by a detector without calorimetric filtering. The broad band emission of the blue light emitted overlaps a small portion of the chlorine dioxide light absorbing region. The overlap in the blue light emission and chlorine dioxide absorbance results in detector responses which are inversely linear to the chlorine dioxide concentration.

A further object of the present invention is to simplify the electrical requirements of the analyzer. Monochromatic light measurements afforded by commercially available analyzers result in logarithmic responses which must be converted to linear electrical readings. It is an object of the present invention to provide an inverse linear response to chlorine dioxide at high concentrations which simplifies amplification circuits and expands the chlorine dioxide measurement range.

Other objects and aspects of the present invention will become apparent to one of ordinary skill in the art on a review of the specification, drawings and claims appended thereto.

SUMMARY OF THE INVENTION

According to a first embodiment of the present invention, a novel method of photometrically analyzing a dilute solution containing chlorine dioxide is provided. The method includes introducing a sample flow into a conduit of a chlorine dioxide analyzer. At least one light emitting diode, in communication with the sample flow, is turned on and off to pass a light beam through the sample. Upon passing through the light beam through the sample the unabsorbed light is received onto a beam splitter which separates the light into a transmitted and a reflected light. The transmitted light is directed through a filter to a first detector which measures the low concentration chlorine dioxide and the reflected light is directed to a second detector which measures a high concentration of chlorine dioxide.

The photometrical analysis process allows for the transmitted light to the first detector to accurately measure chlorine dioxide at a concentration range to the sub part per million level without the use of additional reagents. The reflected light measured by the second detector accurately monitors the concentration of chlorine dioxide as the amount thereof increases in the sample flow.

According to another embodiment of the invention, a light beam emitted from a light emitting diode is passed through a sample flow in the chlorine dioxide analyzer and received onto a detector. This analytical process allows measurement of high chlorine dioxide levels without employment of interference or color filters.

According to a further embodiment of the invention an apparatus for photometrically analyzing a dilute solution is provided. The apparatus includes a chlorine dioxide analyzer having a conduit through which the sample flow is continuously passed. At least one light entry port and a light exit port are diametrically opposed from one another and a light beam generated by a light emitting diode is passed through the sample. At least one detector is utilized to measure the light beam that has passed through the dilute solution as described above.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 1:
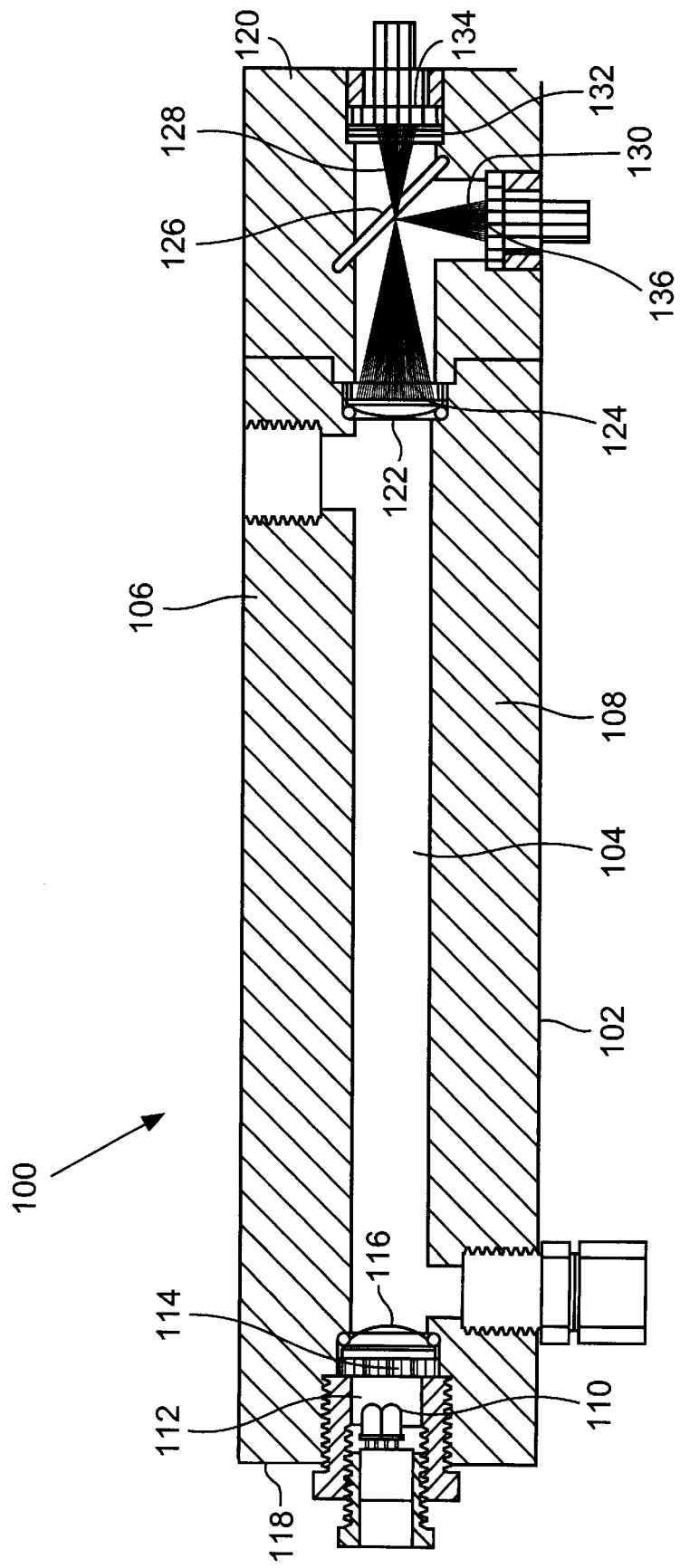
FIG. 1 is an elevated sectional view of a photometric analysis apparatus according to a first embodiment of the invention.
Figure 2:
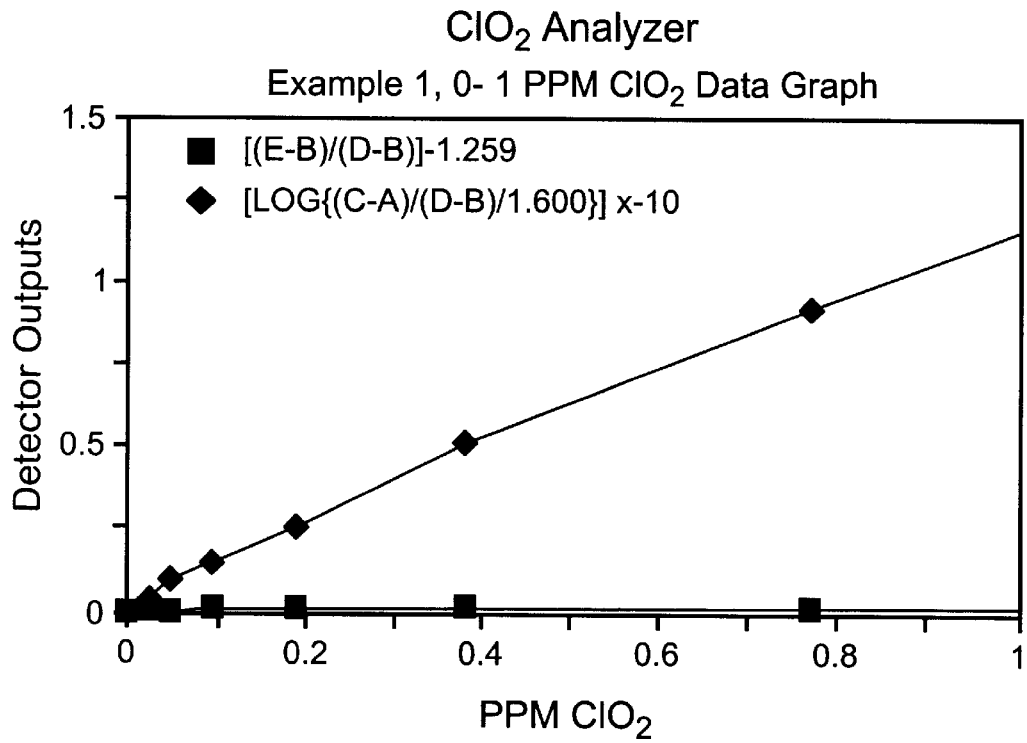
FIGS. 2–5 is a graphical illustration of Example 1 data, wherein the detector outputs is represented on the abscissa and the chlorine dioxide concentration is represented on the ordinate.
Figure 3:
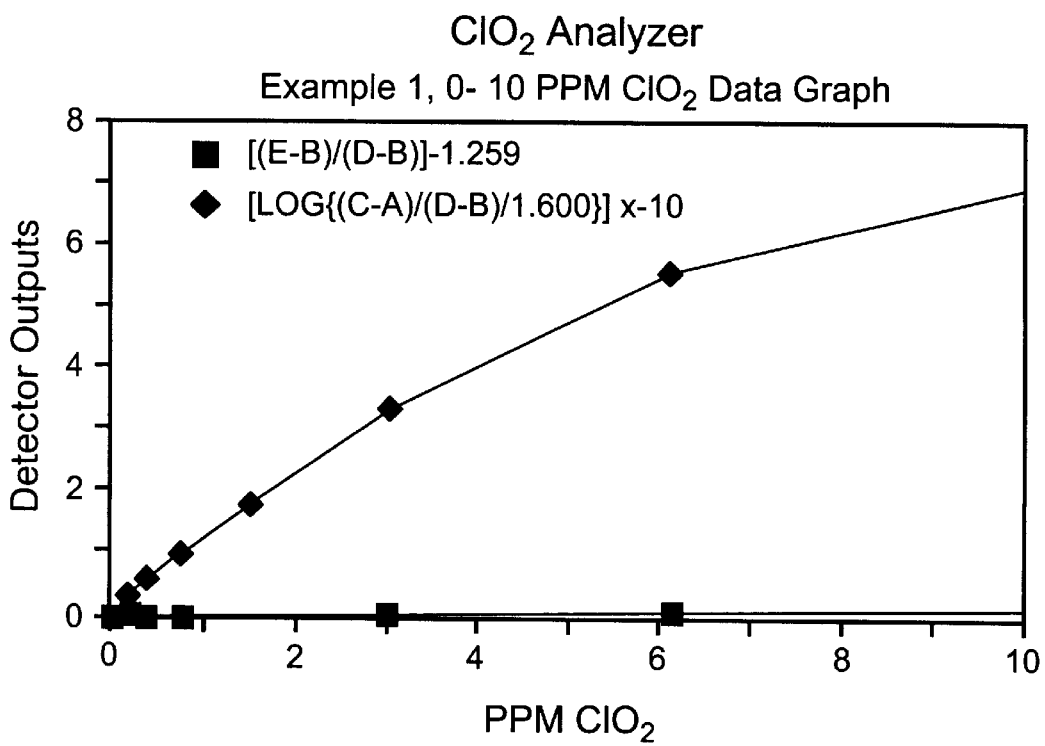
Figure 4:
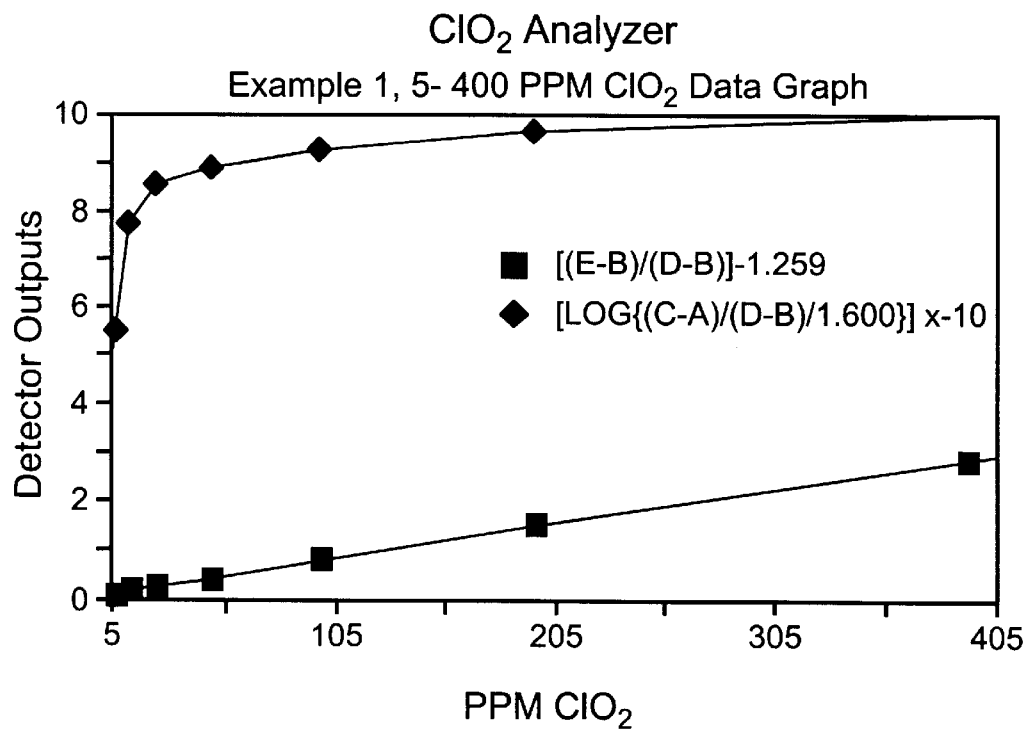
Figure 5:
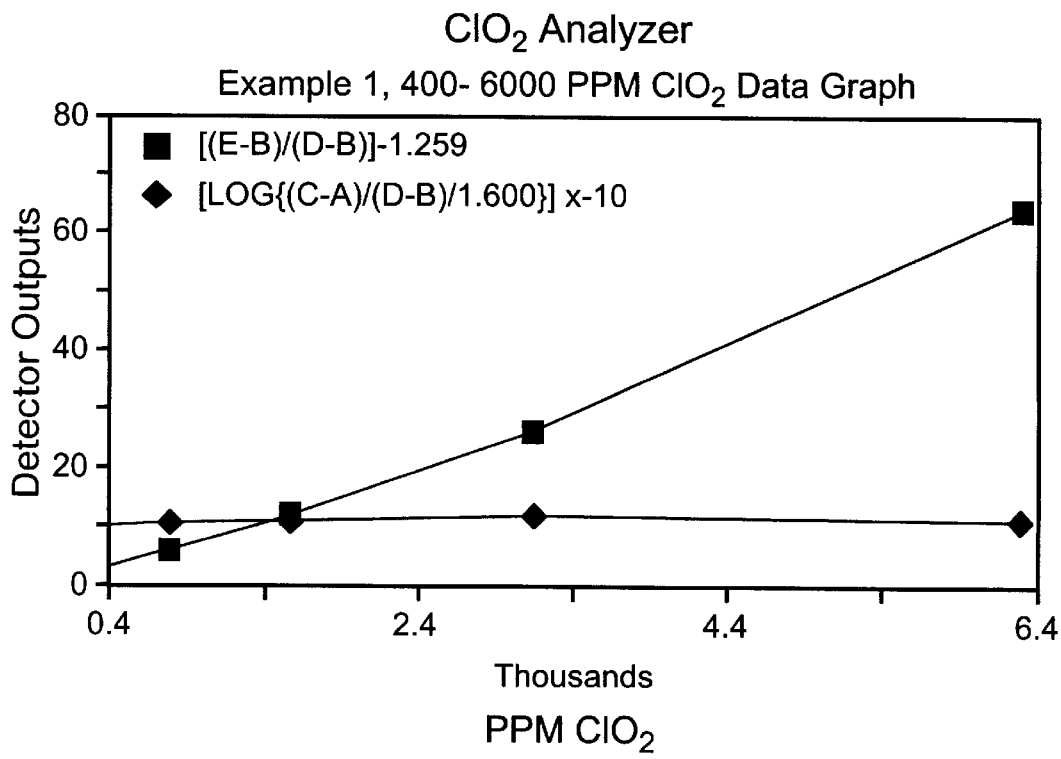

FIG. 1 illustrates a sectional view of a photometric analysis apparatus employed in the first embodiment to measure chlorine dioxide solutions. While the apparatus is exemplary, it should be clear that the inventive concepts described hereinbelow are in no way limited thereto, and can be readily applied to other form of solutions regardless of the state they are in.

Apparatus 100 includes chlorine dioxide analyzer 102 having a sample flow region 104 bounded by top wall 106 and bottom wall 108. The chlorine dioxide analyzer as defined herein is known to one skilled in the art to encompass colorimeters or spectrophotometers.

A blue light emitting diode 110 in conjunction with a red light emitting diode 112, such as the ones sold by Digi-Key under the model numbers P466-ND and P301-ND respectively, are disposed on one end 118 of analyzer 102. The light beam generated by the diodes is collimated prior to reaching the solution and passed through plexiglass lens 114 and a glass lens 116 successively to the sample region. Collectively they are referred to as the entry port. Plexiglass lens 114 is mounted between the sample flow 102 and the glass lens 116 so as to reduce the moisture condensation on the lens.

As the collimated light beam travels through the sample region, part of the light beam is absorbed by the solution, while the rest is communicated to an exit port. The exit port located at opposite end 120 of analyzer 102 includes a glass lens 122 and plexiglass lens 124 disposed in succession. The exiting light beam is received onto a beam splitter 126 which is in line with the exit port. The beam splitter 126 separates the light beam into a transmitted light beam 128 and a reflected light beam 130. Suitable beam splitters include a flat window glass cut wider than the light exit port, placed at a 45° angle to reflect a portion of the light.

Transmitted light 128 is directed through a 410 nm interference filter 132, such as the one sold by Edmund Scientific under model number A 43,105, to a first detector 134, wherein the transmitted 410 nm light beam is utilized to measure low chlorine dioxide levels. The response of the detector is calculated in a logarithmic fashion with respect to the amount of chlorine dioxide concentration present in the sample. The reflected light 130, is directed to a second detector 136, without modification, and it is employed in measuring a high chlorine dioxide concentration. Suitable for use as detectors 134 and 136 are devices sold by Edmund Scientific under model number 10DP/SB 9808-1. The response of detector 136 measured is inversely proportional to the amount of chlorine dioxide present in the sample.

Shown in Example 1, below a solution containing 6290 ppm (parts per million) chlorine dioxide was analyzed, the solution was then diluted with an equal portion of purified water to reduce the chlorine dioxide concentration in half and reanalyzed it. Sequentially thereafter, the solution was diluted by one half and reanalyzed until the solution contained 0.024 ppm chlorine dioxide. Purified water was also analyzed in order to correct the readings obtained.

Detector 134 is employed to measure variables A and C which provide a logarithmic result in the 0.1 to 10 ppm range and detector 136 measures variables B, D and E and provides inverse linear results in the 10 to 5000 ppm chlorine dioxide range. These variables in relation to the detectors are further addressed below.

The blue and red light emitting diodes (110 and 112) are turned on and off with subsequent measurement of the reflected and transmitted light beams. As the blue light is passed through the sample it is partly absorbed by the solution prior to reaching the exit port. On the other hand, the red light would not be absorbed unless it were to encounter contaminants. Contaminants as used herein are known to include bubbling, turbidity, lens fouling, impurities or any other non-dissolved components in the solution. Thus, any change in the red light is utilized to adjust the blue light measured. Table 1, below is demonstrative of the calculations obtained based on the variables measured.

Chlorine Dioxide Analyzer
Example 1 Data
Calculations

| | #1 | #2 | #3 | #4 | |
|---|---|---|---|---|---|
| | Chlorine Dioxide High Range | | | Chlorine Dioxide Low Range | |
| ClO2 PPM | (E – B)/ (D – B) | [(E – B)/ (D – B)] –1.259 | [(C – A)/ (D – B)] | [(C –A)/ (D – B)] /1.600 | {LOG[(C – A) /(D – B)] /1.600}× –10 |
| 0.000 | 1.259 | 0.0000 | 1.600 | 1.000 | 0.000 |
| 0.024 | 1.269 | 0.0100 | 1.590 | 0.994 | 0.027 |
| 0.048 | 1.259 | 0.0000 | 1.570 | 0.981 | 0.082 |
| 0.096 | 1.271 | 0.0120 | 1.550 | 0.969 | 0.138 |
| 0.190 | 1.271 | 0.0120 | 1.510 | 0.944 | 0.251 |
| 0.380 | 1.274 | 0.0150 | 1.420 | 0.888 | 0.518 |
| 0.770 | 1.280 | 0.0210 | 1.290 | 0.806 | 0.935 |
| 1.540 | 1.289 | 0.0300 | 1.070 | 0.669 | 1.747 |
| 3.070 | 1.307 | 0.0480 | 0.749 | 0.468 | 3.296 |
| 6.150 | 1.339 | 0.0800 | 0.446 | 0.279 | 5.548 |
| 12.300 | 1.399 | 0.1400 | 0.269 | 0.168 | 7.744 |
| 24.600 | 1.502 | 0.2430 | 0.223 | 0.139 | 8.558 |
| 49.200 | 1.658 | 0.3990 | 0.205 | 0.128 | 8.924 |
| 98.300 | 2.058 | 0.7990 | 0.189 | 0.118 | 9.277 |
| 197.000 | 2.7855 | 1.5265 | 0.172 | 0.108 | 9.686 |
| 393.000 | 4.167 | 2.9080 | 0.158 | 0.099 | 10.055 |
| 786.000 | 7.042 | 5.7830 | 0.136 | 0.085 | 10.706 |
| 1573.000 | 13.477 | 12.2180 | 0.121 | 0.076 | 11.213 |
| 3150.000 | 27.855 | 26.5960 | 0.099 | 0.062 | 12.107 |
| 6290.000 | 65.79 | 64.5310 | 0.100 | 0.063 | 12.041 |

Calculations
A - Detector #1 Dark Signal, B = Detector #2 Dark Signal, C = Blue LED 15 mA Signal D = Blue LED 0.3 mA Signal, E = Red LED
1 (E – B)/(D – B) Red LED Signal/Blue LED Signal (0.3 mA); B will be close to 0; corrects for bubbles
2 [(E – B)/(D – B)] – 1.259 Corrects for water (0 ppm ClO$_2$) reading; water (E – B)/(D – B) = 1.259
3 (C – A)/(D– B) Blue LED Signal (15 mA)/Blue LED Signal; A will be close to 0; corrects for bubbles
4 [(C – A/(D – B))/1.600 Corrects for water (0 ppm ClO$_2$) reading; water (C – A)/(D – B) = 1.600
5 {LOG[(C – A)/(D – B)]/1.600} × –10 Generates 0 intercept and magnifies data for easier graph comparisons In calculation number one, the blue light is reflected to detector 136 where it is received and converted to a millivolt reading. The value obtained by detector 136 when the blue light is turned off is subtracted therefrom to obtain the actual reading. Subtracting this value, in effect, operates as a calibration of the detector.

Simultaneously, the same operation is carried out for the red light. The ratio of the red light detected to the blue light, provides an accurate reading of the blue light, while accounting for any contaminants in the solution.

At high concentrations (for example, 10 ppm or above), detector 134 does not detect any incoming blue light. As the concentration is sequentially reduced below this reference point, a broad spectrum blue light is emitted by diode 110 (15 mA signal) and detector 134 senses the incoming light through filter 132. At low levels, light in the 400–420 nm range is absorbed in a manner permitting measurement of chlorine dioxide logarithmically.

Due to the high absorbance of light in this spectrum range it is necessary to operate the light at 15 mA in order to transmit a light ray of sufficient intensity for detector 134 to sense the unabsorbed light. The unabsorbed light appears purple in color and is measured when diode 110 is in both the on and off position in order to calibrate detector 134.

On the other hand, most of the blue light emitted by diode 110 in the rest of the spectrum (421–580 nm) is not absorbed by the solution at these same low concentration levels and it is reflected to detector 136. Due to the large amount of unabsorbed blue light, the current supplied to detector 110 is reduced to 0.3 mA, thereby reducing the intensity of the light. However, should the blue light reflected to detector 136 encounter any contaminants part of the blue light would be absorbed. Thus, calculation number three is carried out in similar fashion as the first calculation and provides a ratio of detector 134's reading to that of detector 136 at low level concentrations, while accounting for contaminants.

Calculation numbers two and four are simply the same as the first and third respectively, wherein a correction for pure water is made.

Calculation five is generated to simplify the graphical representation of chlorine dioxide versus the detector outputs as shown in FIGS. 2–5. As noted therein, FIGS. 2–5 depict calculations two and five as the chlorine dioxide is increased progressively. Particularly, the squares represent variables B, D, and E measured by detector 136. The diamonds represent variables A and C measured by detector 134. It is demonstrated from the calculations and graphical depiction that detector 136 provides an inversely linear response in the 10 to 5000 ppm chlorine dioxide range and detector 134 provides logarithmic results in the 0.1 to 10 ppm chlorine dioxide range. Further, as the concentration reaches the 5 to 400 ppm range, the inversely linear results line begins to change its slope, while the logarithmic slope flattens out. This illustration is indicative of the facile employment of a blue light emitting diode in conjunction with a detector in order to obtain inversely linear results without utilization of interference filters.

Figure 6:
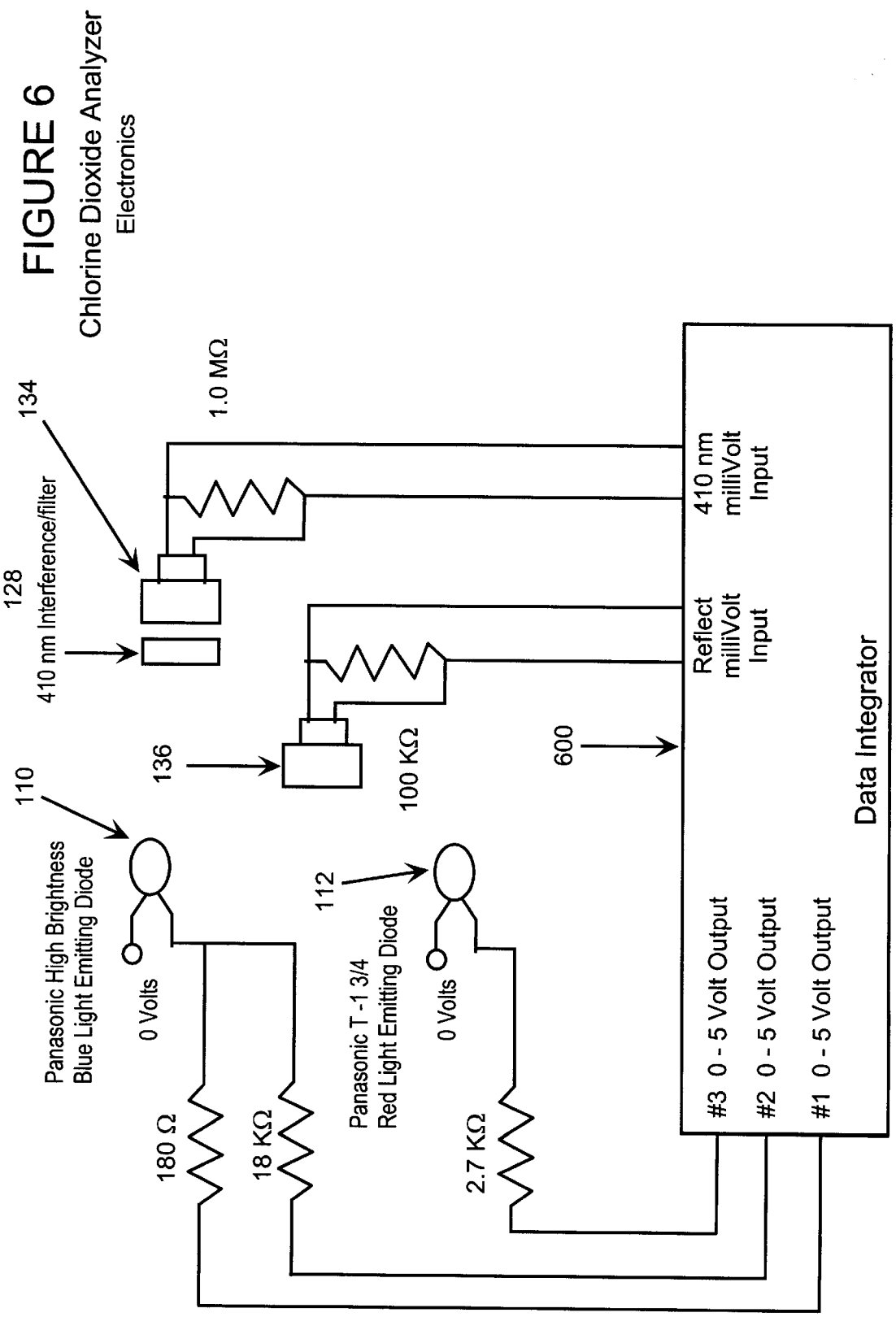
FIG. 6 is a schematic electrical diagram, according to the first embodiment of the invention.

In FIG. 6, a schematic diagram of an electrical implementation device in accordance with the first embodiment is shown. Signals are carried on various lines from data integrator 600 to the light emitting diodes. An output signal of 0–5 volts is transmitted through a 2.7 KΩ resistor to the red light emitting diode 112, depending on whether the operator desires to turn the diode on or off. A similar signal of 0–5 volts is transmitted to the blue light emitting diode 110 via a line containing an 18 KΩ or a line having a 180Ωresistor to obtain the desired light intensity to be emitted. The light is passed through the sample flow and received onto detectors 134 and 136 as described above.

The light signals sensed by detectors 134 and 136 are sent via two respective lines having a 1.0 MΩ and a 10 kΩ resistor to data integrator 600 where the signals are converted into millivolt inputs, facilitating the above calculations.

Figure 7:
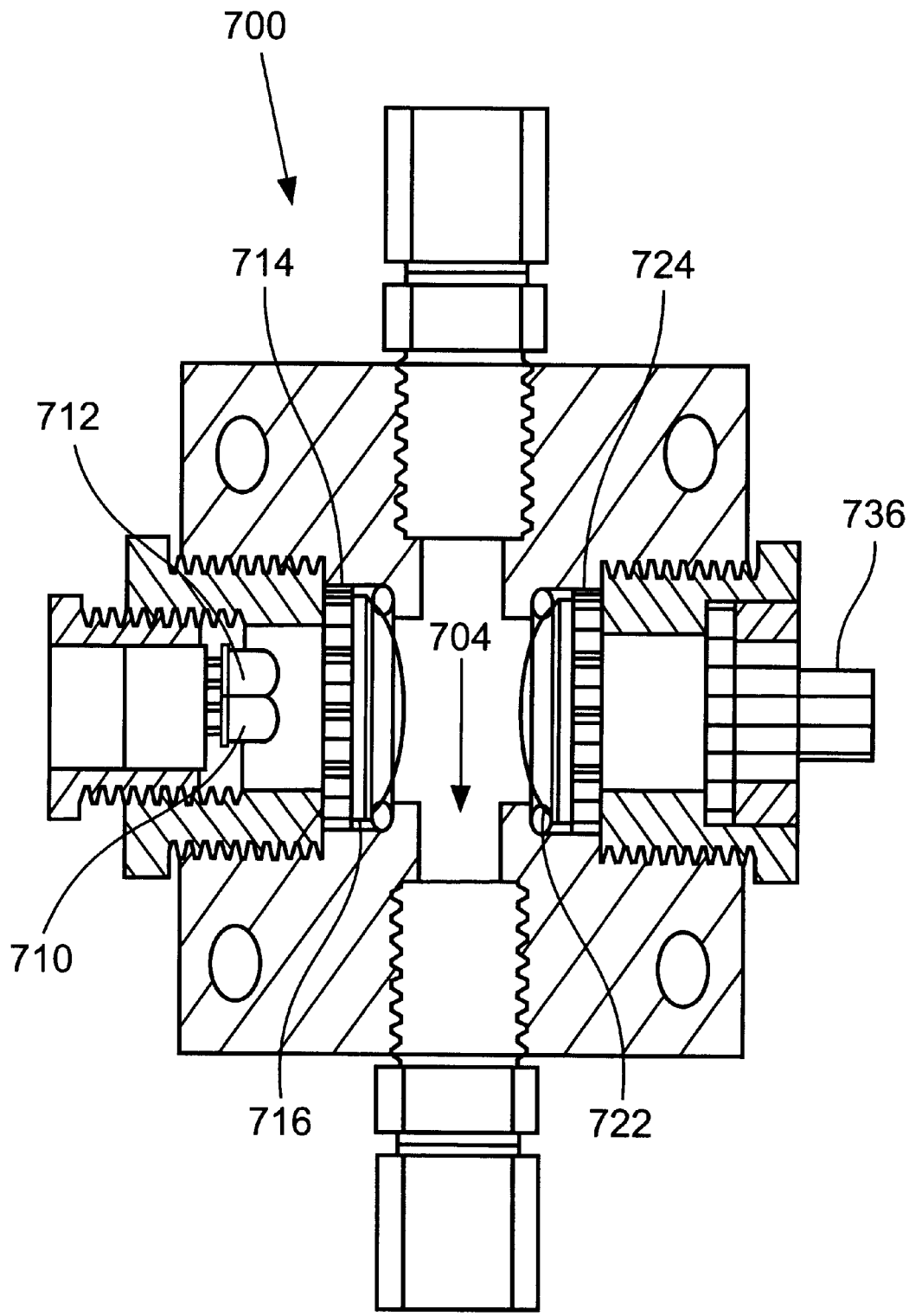
FIG. 7 is an elevated sectional view of a photometric analysis apparatus according to a second embodiment of the invention.

FIG. 7 illustrates a second embodiment of an optical design which is simpler and more reliable than commercially available chlorine dioxide analyzers. Similarly to the embodiment described above, analyzer 700 includes blue and red light emitting diodes 710 and 712, respectively. At chlorine dioxide concentrations ranging from 20 to 9,000 ppm, the light is collimated and passed through an entry port formed by a plexiglass lens 714 and glass lens 716 in succession. These types of glass lenses are sold by Edmund Scientific under model number A 45,097.

As the collimated light passes through sample region 704, part of the light beam is absorbed by the solution, and the rest exits through a port diametrically opposed to the entry port. The unabsorbed light passes through glass lens 722 and plexiglass lens 724 and strikes detector 736.

Similarly to the analysis conducted with reference to the first embodiment, in Example 2, a solution of 9230 ppm chlorine dioxide in purified water was analyzed. The solution was subsequently diluted a number of times with purified water to reduce the concentration in half each time until the solution contained 4.5 ppm chlorine dioxide. Purified water was also tested to account for this reading in the measurements. The compiled data is shown in Table 2, below.

TABLE 2

Chlorine Dioxide Analyzer
Example 2 Data
Calculations

| ClO2 PPM | #1 C − A m Volts | #2 1/(C − A) | #3 B − A m Volts | #4 (B − A)/ (C − A) | #5 [(B − A)/ (C − A)] −0.93072 |
|---|---|---|---|---|---|
| 0.0 | 19.213 | 0.05205 | 17.882 | 0.930724 | −0.000000 |
| 4.5 | 19.184 | 0.05213 | 17.917 | 0.936770 | 0.006048 |
| 9.0 | 19.143 | 0.05224 | 17.953 | 0.937836 | 0.007112 |
| 18.0 | 19.022 | 0.05257 | 18.060 | 0.949427 | 0.018703 |
| 36.0 | 17.780 | 0.05325 | 18.055 | 0.961395 | 0.030671 |
| 72.1 | 18.357 | 0.05448 | 17.958 | 0.978264 | 0.047540 |
| 144.0 | 17.594 | 0.05684 | 18.010 | 1.023644 | 0.092920 |
| 216.0 | 16.892 | 0.05920 | 17.936 | 1.061804 | 0.131080 |
| 288.0 | 16.221 | 0.06165 | 18.040 | 1.112139 | 0.181415 |
| 433.0 | 15.091 | 0.06626 | 17.858 | 1.183354 | 0.252630 |
| 577.0 | 14.078 | 0.07103 | 18.021 | 1.280082 | 0.349358 |
| 865.0 | 12.584 | 0.07947 | 17.912 | 1.423395 | 0.492671 |
| 1150.0 | 11.251 | 0.08888 | 18.096 | 1.608390 | 0.677666 |
| 1730.0 | 9.507 | 0.10519 | 17.899 | 1.882718 | 0.951994 |
| 2310.0 | 8.106 | 0.12337 | 18.177 | 2.242413 | 1.311689 |
| 3460.0 | 6.354 | 0.15738 | 17.957 | 2.826094 | 1.895370 |
| 4615.0 | 5.127 | 0.19505 | 18.044 | 3.519407 | 2.588683 |
| 6920.0 | 3.799 | 0.26323 | 17.912 | 4.714925 | 3.784201 |
| 9230.0 | 2.833 | 0.35298 | 18.412 | 6.499118 | 5.568394 |

Calculations
A = Detector Dark Signal, B = Red LED Signal, C = Blue LED Signal
1 C − A Blue LED Signal - Dark Signal; A will be close to 0
2 1/(C − A) inverse of Blue LED Signal - Dark Signal
3 B − A Red LED Signal - Dark Signal
4 (B − A)/(C − A) Ratio of Red to Blue; corrects for bubbles, turbidity and lens fouling
5 (B − A)/(C − A) − 0.93072 Corrects for water (0 ppm ClO2) reading; water (B − A)/(C − A) = 0.93072

As the blue and red lights are turned on and off subsequent measurements are made by detector 736. As discussed above the red light is not absorbed, unless it encounters the aforementioned contaminants. Detector 736 measures variables A, B and C and provides an inversely linear response to the concentration of chlorine dioxide in the sample. The calculations are carried out in a similar manner as in the first embodiment where lens fouling, turbidity and readings in pure water are accounted for.

Figure 8:
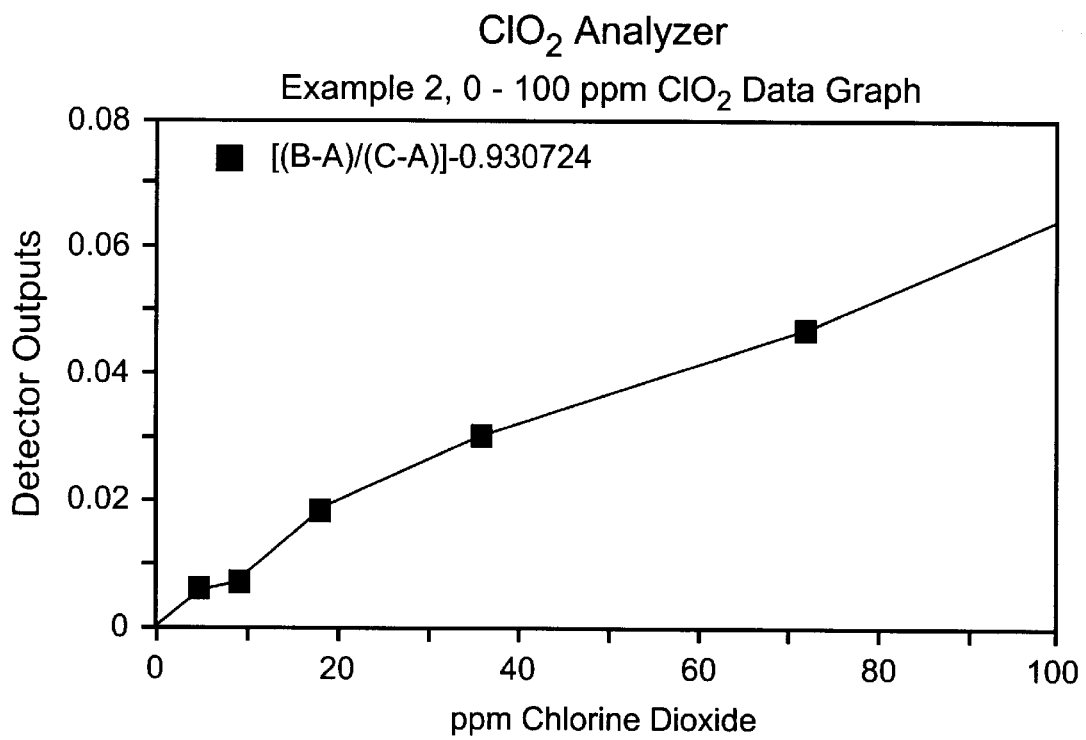
FIGS. 8–10 is a graphical illustration of Example 2 data, wherein the detector output is represented on the abscissa and the chlorine dioxide concentration is represented on the ordinate.
Figure 9:
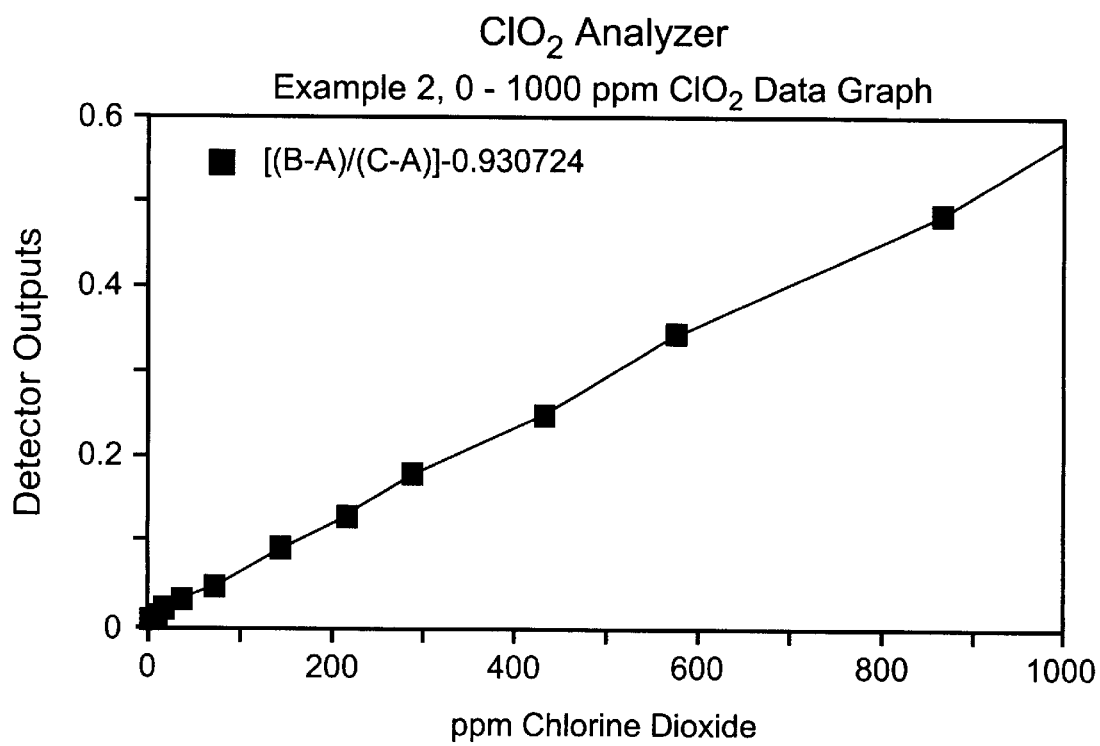
Figure 10:
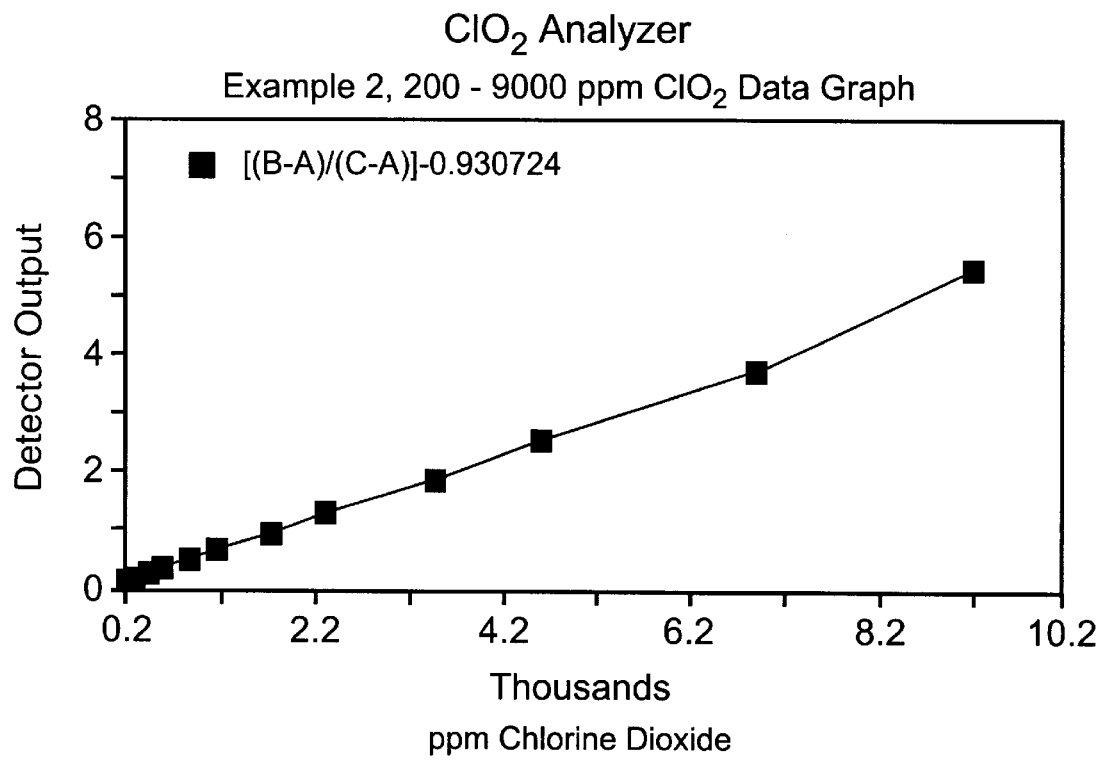

FIGS. 8–10 provide a graphical representation of calculation number five, wherein the inverse blue light signal measurement as adjusted for contaminants and corrected for pure water is plotted. It is noted that from this calculation and the graphical representation that detector 736 provides an inversely linear response to a concentration reading in the 20–9,000 ppm range.

The chlorine dioxide analyzer of the present invention can readily be applied to generators such as the ones sold by Vulcan Chemical Technologies, under model number C500-WMCWS Se# 5602. The analyzer described in the second embodiment, for example can be applied in a facile manner to this type of a generator to obtain a rudimentary reading of the concentration without the necessity of a microprocessor.

Figure 11:
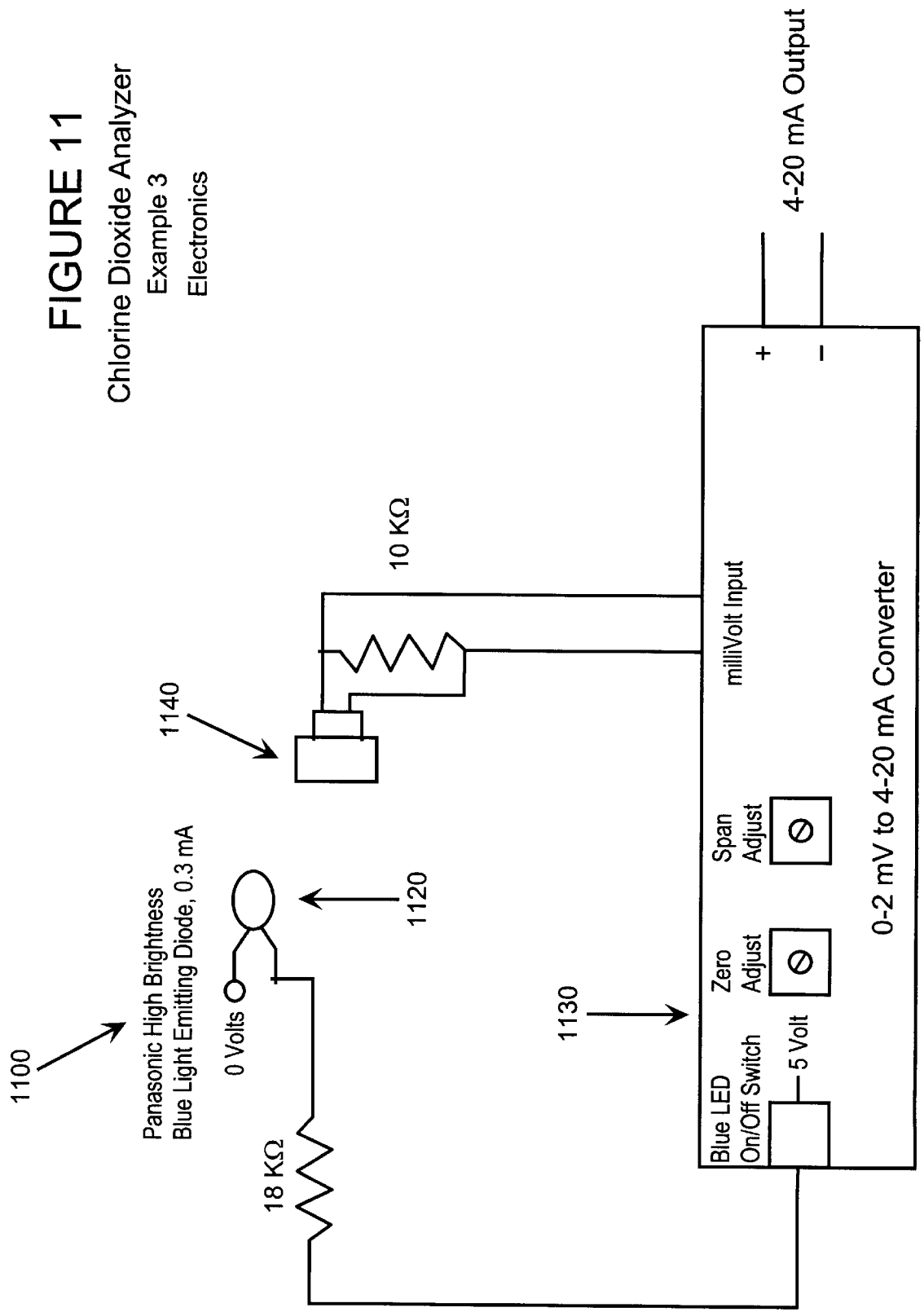
FIG. 11 is a schematic electrical diagram, according to the second embodiment, Example 3 of the invention.

With reference to FIG. 11, the schematic diagram 1100 of an analyzer attached to a generator outlet is presented. To optimize the conversion to chlorine dioxide, appropriate amounts of sodium chlorite and chlorine are mixed and produced in the generator. It is an important objective in generating the solution to eliminate any measurable content of the above mentioned compounds from the final product. Therefore, by simply monitoring the chlorine dioxide concentration within the generator outlet, changes to the chlorine feed rate or the other components can be made.

In an exemplary embodiment, a single blue light detector 1110 is connected to a 0–2 mV to 4–20 mA converter 1130. Utilizing blue light emitting diode 1120, the zero point is adjusted in pure water until a 4.00 mA output is obtained when the diode is in the off position. On the other hand, when the diode is in the on position, light is passed through the sample flow of purified water until a reading of 20.00 mA is obtained. Thus, a span of 4–20 mA is attained. The blue light is, therefore, implemented to control the feeding rate of the components based on the determined concentration of chlorine dioxide which falls within the output span.

Figure 12:
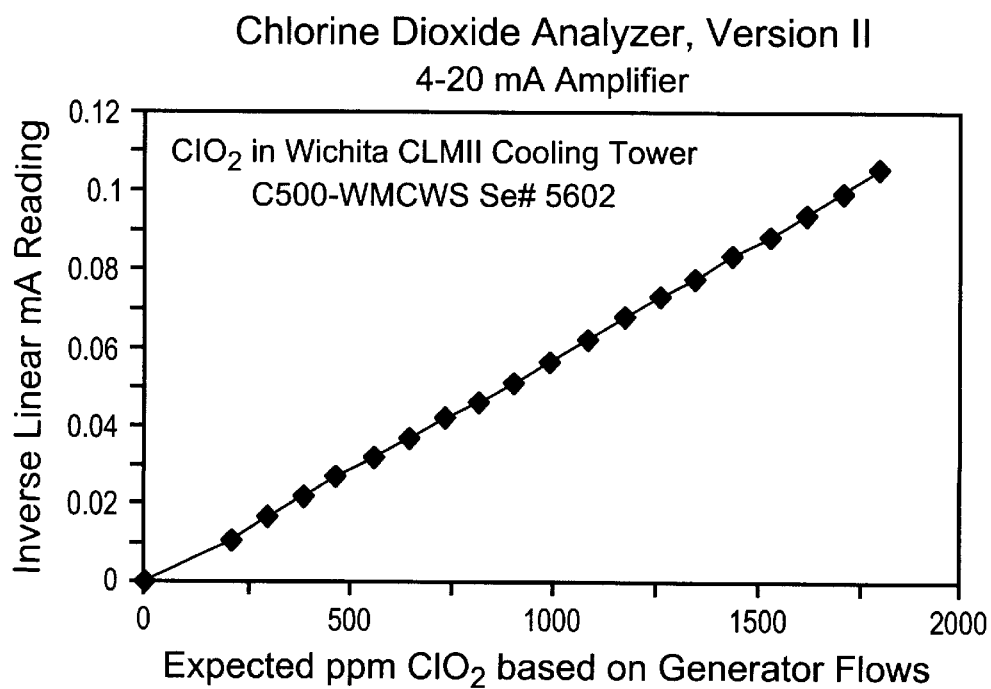
FIG. 12 is a graphical illustration of Example 3 data, wherein the detector output is represented on the abscissa and the chlorine dioxide concentration is represented on the ordinate.

As shown in Example 3, detector 1100's response is inversely proportional relationship to the amount of chlorine dioxide generated. The calculations and results are tabulated in Table 3 below and shown graphically in FIG. 12.

TABLE 3

Chlorine Dioxide Analyzer
Example 3 Data

| Expected by Flows ClO2 PPM | Output mA | [1/mA − 4)] − (1/14.30) |
|---|---|---|
| 0 | 18.30 | 0.000000 |
| 210 | 16.42 | 0.010585 |
| 296 | 15.55 | 0.016650 |
| 386 | 14.90 | 0.021813 |
| 466 | 14.30 | 0.027157 |
| 559 | 13.81 | 0.032007 |
| 649 | 13.35 | 0.037022 |
| 736 | 12.91 | 0.042303 |
| 819 | 12.59 | 0.046484 |
| 906 | 12.25 | 0.051282 |
| 996 | 11.88 | 0.056973 |
| 1089 | 11.54 | 0.062696 |
| 1179 | 11.22 | 0.068574 |
| 1266 | 10.96 | 0.073748 |
| 1348 | 10.75 | 0.078218 |
| 1439 | 10.48 | 0.084391 |
| 1532 | 10.29 | 0.089052 |
| 1622 | 10.07 | 0.094815 |
| 1712 | 9.88 | 0.100138 |
| 1802 | 9.67 | 0.106437 |

It is noted that the third column represents the inversely proportional output to the concentration of chlorine dioxide in the solution. The (mA-4) connotes a correction for the 4 mA lower limit, obtained in pure water, thereby zeroing the convertor's measurement. The subtracted (1/14.30) portion of the calculation represents the correction for the output value obtained in pure water. Thus, as shown graphically in FIG. 12, an inversely linear relationship between the detector's output and the concentration of chlorine dioxide is obtained in a simple and effortless manner.

While the invention has been described in detail with reference to specific embodiments thereof, it will be apparent to one skilled in the art that various changes and modifications can be made, and equivalents employed, without departing from the scope of the appended claims.

What is claimed is:

1. A method of photometrically analyzing a dilute solution containing chlorine dioxide and comprising the steps of:
    (a) introducing a sample flow into a conduit of a chlorine dioxide analyzer;
    (b) turning at least one light emitting diode on and off and when in the on position a light beam is emitted from the diode and passed through the sample;
    (c) receiving said emitted light that has passed through the sample onto a beam splitter, wherein said light beam is separated into a transmitted light and a reflected light;
    (d) directing the transmitted light through a filter to a first detector and directing the reflected light to a second detector, and
    (e) determining the chlorine dioxide concentration by detecting a non-monochromatic blue light emitted by one of said light emitting diodes and measuring the inversely proportional response of said second detector without logarithmic conversion.

2. A method according to claim 1, wherein the chlorine dioxide analyzer comprises a first and second light emitting diode.

3. A method according to claim 2, wherein one of said diodes emits a blue light and the other said diode emits a red light.

4. A method according to claim 3, wherein said blue and red light are collimated prior to reaching the solution.

5. A method according to claim 3, further comprises measuring said reflected and said transmitted light to determine the chlorine dioxide concentration while correcting for contaminants.

6. A method according to claim 5, wherein said transmitted light detected by said first detector measures a low chlorine dioxide concentration.

7. A method according to claim 6, wherein said transmitted light is measured by said first detector and a logarithmic response to the amount of chlorine dioxide present in the solution is provided.

8. A method according to claim 5, wherein said reflected light detected by said second detector measures high chlorine dioxide concentration levels.

9. A method according to claim 5, wherein said reflected light is measured by said second detector and a inversely proportional response to the amount of chlorine dioxide present in the solution is provided.

10. A method according to claim 1, wherein said filter is a 410 nm interference filter.

11. A method of photometrically analyzing a dilute solution containing chlorine dioxide and comprising the steps of:
    (a) introducing a sample flow into a conduit of a chlorine dioxide analyzer;
    (b) turning at least one light emitting diode on and off and when in the on position a light beam is emitted from said diode and passed through the sample;

(c) receiving said emitted light by a detector; and (d) determining the chloride dioxide concentration by detecting a non-monochromatic blue light emitted by one of said light emitting diodes and measuring the inverse proportional response of said second detector without logarithmic modification.

12. A method according to claim 11, wherein the chlorine dioxide analyzer comprises a first and a second light emitting diode.

13. A method according to claim 12, wherein one of said diodes emits a blue light and the other said diode emits a red light.

14. A method according to claim 13, wherein said blue and red light are collimated prior to reaching said detector.

15. A method according to claim 14, wherein said blue and red light received by said detector measures a high concentration level of chlorine dioxide while correcting for contaminants.

16. A method according to claim 14, wherein said blue light received by said detector and corrected for fouling, bubbling and impurities is inversely proportional to the amount of chlorine dioxide present.

17. An apparatus for photometrically analyzing a dilute solution of chloride dioxide, comprising:

(a) a chlorine dioxide analyzer having a conduit through which the sample flow is continuously passed;

(b) at least one light entry port and a light exit port diametrically opposed therefrom, each said port being in communication with said sample flow and containing a light transmissive window;

(c) at least one light emitting diode for generating a light beam which is passed through said sample flow;

(d) at least one detector for measuring said light beam exiting said sample flow through said exit port, and wherein said light beam measured by said at least one detector is non-monochromatic blue and provides an inversely proportional reading in response to the amount of chlorine dioxide present in the solution without logarithmic modification.

18. An apparatus according to claim 17, wherein the chlorine dioxide analyzer comprises a first and second light emitting diode.

19. An apparatus according to claim 18, wherein one of said diodes emits a blue light and the other said diode emits a red light which are collimated prior to reaching the solution.

20. An apparatus according to claim 19, wherein said light beam is measured by said detector and provides an inversely proportional reading in response to the amount of chlorine dioxide present in the solution.

21. An apparatus according to claim 19, wherein said first detector further comprises a 410 nm interference filter.

22. An apparatus according to claim 21, further comprising a beam splitter disposed between the light exit port and said first detector.

23. An apparatus according to claim 22, wherein the beam splitter transmits a portion of said light beam exiting the exit port to said first detector and reflecting a second portion of said light beam to a second sensor, which is offset from said first detector.

24. An apparatus according to claim 23, wherein said transmitted light is measured by said first detector and provides a logarithmic reading in response to the amount of chlorine dioxide present in the solution.

25. An apparatus according to claim 23, wherein said reflected light is measured by said second detector and provides an inversely proportional reading in response to the amount of chlorine dioxide present in the solution.

26. A generator for the addition and conversion of chemical components to chlorine dioxide, comprising:

(a) a chlorine dioxide analyzer attached to said generator to optimize said conversion, the chlorine dioxide analyzer having a conduit through which the sample flow is continuously passed;

(b) at least one light entry port and a light exit port diametrically opposed therefrom, each said port being in communication with said sample flow and containing a light transmissive window;

(c) at least one light emitting diode for generating a light beam which is passed through said sample flow; and (d) at least one detector for measuring said light beam exiting said sample flow through said exit port, and wherein said light beam measured by said at least one detector is blue non-monochromatic light and provides an inversely proportional reading in response to the amount of chlorine dioxide present in the solution without logarithmic modification.

27. A generator according to claim 26, wherein said diode emits a blue light beam which is collimated prior to reaching the sample flow.

28. A generator according to claim 27, wherein said light beam is measured by said detector and provides an inversely proportional reading in response to the amount of chlorine dioxide present in said sample flow.

29. A method of photometrically analyzing a dilute solution containing chlorine dioxide comprising the steps of:

(a) introducing a sample flow into a conduit of a chlorine dioxide analyzer;

(b) emitting an unfiltered non-monochromatic blue light from a diode through the sample;

(c) receiving the unfiltered blue light by a detector; and (d) determining the chlorine dioxide concentration by using the reciprocal of said detector output without logarithmic modification.

\* \* \* \* \*